United States Patent [19]

Sernetz

[11] Patent Number: 4,968,459

[45] Date of Patent: Nov. 6, 1990

[54] METHOD FOR THE PRODUCTION OF TRANSPARENT, POLYCRYSTALLINE ALUMINA WITH A YELLOWISH COLOR TONE

[75] Inventor: Friedrich Sernetz, Pforzheim, Fed. Rep. of Germany

[73] Assignee: Dentaurum J.P. Winkelstroeter KG, Ispringen, Fed. Rep. of Germany

[21] Appl. No.: 335,108

[22] Filed: Apr. 7, 1989

[30] Foreign Application Priority Data

Apr. 9, 1988 [DE] Fed. Rep. of Germany ....... 3811902

[51] Int. Cl.$^5$ .............................................. B29D 11/00
[52] U.S. Cl. ..................................... 264/1.2; 264/63; 264/66
[58] Field of Search .................... 264/1.2, 2.6, 16, 19, 264/20, 570, 63, 66; 501/127, 153

[56] References Cited

U.S. PATENT DOCUMENTS

| | | | |
|---|---|---|---|
| 3,131,025 | 4/1964 | Carnall, Jr. et al. | 23/135 |
| 3,476,690 | 11/1969 | Carnall, Jr. et al. | 252/300 |
| 3,562,371 | 2/1971 | Bush | 264/65 |
| 3,853,973 | 10/1974 | Härdtl et al. | 264/65 |
| 4,323,545 | 4/1982 | Sellers | 423/625 |
| 4,427,785 | 1/1984 | Prochazka et al. | 501/128 |
| 4,495,116 | 1/1985 | Kaneno et al. | 264/1.2 |
| 4,761,390 | 8/1988 | Hartnett et al. | 501/152 |
| 4,830,994 | 5/1989 | Schuetz | 501/127 |

FOREIGN PATENT DOCUMENTS

| | | |
|---|---|---|
| 177212 | 10/1951 | Austria ................................ 264/20 |
| 0297908 | 2/1979 | European Pat. Off. . |
| 0040499 | 2/1981 | European Pat. Off. . |
| 0030851 | 5/1982 | European Pat. Off. . |
| 3523801 | 3/1972 | Fed. Rep. of Germany . |
| 1244435 | 8/1972 | Fed. Rep. of Germany . |
| 2949512 | 8/1975 | Fed. Rep. of Germany . |
| 658008 | 12/1979 | Fed. Rep. of Germany . |
| 2313760 | 9/1981 | Fed. Rep. of Germany . |
| 62-162669 | 9/1979 | Japan . |

OTHER PUBLICATIONS

G. De With, Preparation, Microstructure and Properties of $Y_3Al_5O_{12}$ Ceramics, 1987.

B. J. Kelleth and Fred F. Lange, Experiments on Pore Closure During Hot Isostatic Pressing and Forging, 1988.

H. U. Kessel, H. Kolaska and K. Dreyer, Manufacture and Properties of Gas-Pressure Sintered Zirconia, 1988.

Sung-Tae Kwon and Doh-Yeon Kim, Effect of Sintering Temperature on the Densification of $Al_2O_3$, Apr. 1987.

*Primary Examiner*—James Lowe
*Assistant Examiner*—Christopher A. Fiorilla
*Attorney, Agent, or Firm*—Reising, Ethington, Barnard, Perry & Milton

[57] ABSTRACT

A method for the production of shaped bodies of transparent polycrystalline alumina having a yellowish color tone. A green body is formed using pure, fine-grained alumina. The auxiliary agents are burned out of the green body. The green body is treated in such a way as to produce a closed surface on the shaped body. The body is compacted to a transparent, polycrystalline alumina body. Finally, the body is annealed in air to impart a yellowish color tone to the body.

28 Claims, No Drawings

METHOD FOR THE PRODUCTION OF TRANSPARENT, POLYCRYSTALLINE ALUMINA WITH A YELLOWISH COLOR TONE

The invention relates to a method for the production of shaped bodies of transparent, polycrystalline alumina, wherein a green body is formed in a first step using pure, fine-grained alumina with a purity of >99.0%, wherein, in the given circumstances, the green body is freed from the auxiliary agents used in the production by burning-out in a second step, wherein pretreatment is carried out as a subsequent third step, and wherein the compaction to transparent, polycrystalline alumina takes place in a fourth step.

Such a method is known from the literature of R. L. Coble ( J. Amer. Ceram. Soc. 45, 123–127 (1962) and from U.S. Pat. No. 3,026,210. In this method, alumina is doped with up to 0.5% magnesia in order to prevent pronounced, undesired grain growth during the sintering and to thus improve the transparency of the sintered material. In accordance with this method, a precompacted green body was customarily presintered in an oxygen-containing atmosphere in the temperature range of from 1000 to 1200 degrees C. and subsequently dense sintered in a hydrogen atmosphere or in a vacuum at temperatures of between 1700 and 1950 degrees C.

A method for the production of transparent, polycrystalline alumina is known from U.S. Patent No. 3,899,560 wherein, however, a purity of the alumina of at least 99.97% is required and wherein the shaped bodies are hot forged at temperatures above 1800 degrees C. Doping is not necessary in this method, but shaped bodies with complex structures, which are desired, in particular for orthodontic parts, are not attainable on account of the hot forging.

According to currently accepted opinion (cf. E. Doerre, H. Huebner "Alumina", Springer publishing house 1984, page 229 ff.) it is important in the production of polycrystalline, transparent alumina to eliminate the residual porosity in the shaped body in order to minimize the number of reflecting and hence scattering boundaries in the product.

In the methods hitherto, this was achieved by selecting relatively low temperatures, i.e., temperatures in the range of from 1000 to 1200 degrees C. for the presintering in order to obtain a pore structure which is open right up to the surface, resulting in a continuous, open pore structure in the presintered shaped body. A very high temperature, i.e., above 1700 degrees C. is then used for the second sintering, also referred to as dense sintering.

If this high-temperature sintering was carried out in the presence of air, i.e., in a substantially nitrogen-containing atmosphere, a residual porosity was left over in the alumina, which was explained by the insolubility of nitrogen and other inert gases in alumina. For this reason, the dense sintering was hitherto carried out either in a hydrogen atmosphere because hydrogen exhibits a limited solubility in alumina or in a vacuum, thereby preventing the formation of occlusions of gas in the shaped alumina body during the dense sintering.

However, these methods all have the disadvantage that the final sintering must be carried out at very high temperatures. Because of the necessary high temperatures and either the required hydrogen atmosphere or the required vacuum, very complicated and expensive furnace equipment is needed, which, in all, makes the method uneconomical and unsuitable for general application.

The object of the invention is to suggest a method with which also shaped bodies having complex structures can be produced at lower temperatures and under more economical environmental conditions.

This object is achieved, in accordance with the invention, in a method of the kind described at the beginning by a closed surface being produced on the shaped body during the pretreatment and by pressure from all sides at elevated temperature being used in the fourth step to compact the shaped body, whereby the residual porosity inside the shaped body is closed.

The closed surface of the shaped body is to be regarded as gas-tight with respect to normal oxygen-containing atmospheres such as, for example, air so that the gas enclosed in the shaped body cannot simply escape to the outside or be exchanged during the dense sintering as in Coble's method.

The inventive method deliberately breaks away from the methods hitherto wherein special care was taken to ensure that the pretreatment produced shaped bodies with an open porosity, i.e., that in the pretreatment a connection was maintained from the pores inside the shaped body outwardly towards the surface of the shaped body, and requires that a closed surface i.e., that no connections are maintained from the pores inside the shaped body outwardly toward the surface thereof, be produced on the shaped body. In view of this closed surface of the shaped body, the atmosphere in which the dense sintering is carried out in the fourth step is essentially unimportant and so the gas atmosphere surrounding the shaped body may be selected purely according to criteria which are most advantageous for the apparatus used.

In preferred methods, the pretreatment of the green body will comprise presintering.

The presintering is preferably carried out in such a way that the holding times in the presintering temperature range are as short as possible in order to keep grain growth in the shaped body to a minimum.

Pretreatment has proven particularly expedient wherein the melting of the surface is carried out by means of laser light because the action can then be concentrated with high precision on the surface region only of the shaped body, and wherein a sudden temperature increase can be achieved in the treated surface region. Also, with such method performance, the undesired grain growth, in particular also inside the shaped body, is reduced to a minimum.

A further advantage of the inventive method is that alumina without doping can now be used. However, alumina powders to which doping material has been added may, of course, also be processed with the inventive method.

The alumina powder itself is preferably used with a purity of ≧99.7%.

Further preferred are alumina powders with a purity of ≧99.9%, which produces the best results with respect to transparency.

The temperatures for the presintering of the green body preferably lie above 1400 degrees C., with the green body first being heated up slowly to a temperature of approximately 500 degrees C. in order to burn out of the green body the auxiliary agents which may have been used for its formation. After the auxiliary agent has been fully burned out of the green body, the actual presintering is then initiated by the temperature being raised as rapidly as possible to the sintering temperature. As mentioned previously, in lieu of the presintering, the surface of the shaped body may be melted with laser light.

The preferred temperature range for the presintering in which the required closed porosity is achieved on the surface of the shaped body in a relatively short time is from 1500 degrees C. to 1700 degrees C.

The presintering of the green body is preferably carried out in the presence of an oxygen-containing atmosphere, in particular air. Methods are preferred wherein the heating-up to the actual sintering temperature should, if possible, take place at $\geq 30$ degrees C./min, with the sintering temperature then being held for approximately 30 minutes.

In a preferred method according to the invention, the compacting of the shaped body in the third method step is achieved by hot isostatic pressing.

Alternatively, it is conceivable to use pressure-assisted sintering or PAS which is likewise carried out at quite high temperatures, but pressures of up to 100 bar at the most are used.

Both techniques are equally well usable in the inventive method but pressure assisted sintering has the advantage that the equipment required therefor involves substantially lower costs because it does not have to withstand extreme pressures.

A great advantage of the inventive method over the methods known from the prior art is to be seen in that the temperature during the hot isostatic pressing need only lie above 1000 degrees C., with satisfactory transparency of the shaped bodies already being attained for many fields of application, for example, for orthodontic brackets where a certain residual opacity is indeed desired in order to bring the shaped bodies closer in appearance to the color of the teeth.

Above 1400 degrees C., excellent transparency is already obtained.

However, most preferred are temperatures for the dense sintering during the hot isostatic pressing in the range of from 1500 degrees C. to 1700 degrees C. as shorter holding times at the dense sintering temperature can be used.

It is expedient for the hot isostatic pressing to be carried out in a protective gas atmosphere. The protective gas atmosphere is not of importance to the shaped body as it could also be dense sintered in an oxygen-containing atmosphere, but to the material of the autoclave or, quite generally, to the dense sintering apparatus used. In contrast therewith, the prior art is always dependent on a protective gas atmosphere, in particular a reducing atmosphere such as, for example, hydrogen gas as it is important there for the sintering atmosphere to contain gases which exhibit at least a partial solubility in the shaped body material.

The gas pressure during the dense sintering will preferably be approximately 1000 bar.

As mentioned previously, the dense sintering may, however, also be carried out by the pressure-assisted sintering method wherein only pressures of up to 100 bar must be used.

In a preferred method, the starting material for the formation of the green bodies is comprised of fine-grained alumina powder with a mean grain size of less than 5 $\mu$m which is mixed with a binder and possibly with doping material and spray-dried to form a granular material with a mean grain size of from approximately 100 $\mu$m to 300 $\mu$m. The shaped bodies produced by this method possess good transparency in the visible range and also in the near-ultraviolet and near-infrared regions.

The choice of grain size of the alumina powder can influence to a certain extent the wavelength range in which the inventive polycrystalline alumina exhibits its maximum transparency.

The thus obtained granular material is, for example, uniaxially compressed to form the desired shaped bodies.

After one of the previously described pretreatments, the polycrystalline shaped bodies are still completely opaque, the transparency only being attained after the dense sintering during which closure of the residual porosity takes place.

The results of this method are surprising in several respects because (a) no dopings of the alumina are required to prevent grain growth;

(b) no vacuum or reducing atmosphere such as, for example, hydrogen is required to avoid the residual porosity; and (c) at distinctly lower temperatures, with the use of (gas) pressure from all sides, compaction is achievable, whereby the existing residual porosity is closed and hence transparency of the shaped body is attained.

With the inventive method, a substantially more economical and more reliable method for producing transparent, polycrystalline alumina is available than hitherto, particularly due to the temperatures during the dense sintering being substantially lower and to a vacuum or a reducing atmosphere being dispensed with in the dense sintering apparatus. Furthermore, the inventive method provides a possibility of producing without doping material shaped bodies of transparent, polycrystalline alumina with a complex structure.

The field of use of transparent alumina which hitherto included, for example, sodium-vapor lamps, may now be extended to a plurality of other fields such as, for example, the manufacture of orthodontic parts, for example, brackets and buccal tubes.

Further interesting fields of use for the shaped bodies produced in accordance with the invention are measuring and testing optics, in particular also in the infrared region, as well as laser optics.

The shaped bodies obtained with the inventive method are also usable in wide temperature ranges. Only from temperatures above 600 degrees C. onwards do slight changes occur, however, these do not affect the transparency of the shaped body but rather its color. In this temperature range, the shaped bodies start to take on a slightly yellowish tone, depending on the temperature and treatment time. This change in color can be brought about with very high precision and is advantageous particularly for shaped bodies in the dental field as they can thus be brought closer in their color to the tooth color.

The stability of the transparency of the shaped bodies produced in accordance with the invention is evident from the fact that they do not lose their transparency up to approximately 1200 degrees C. Therefore, a temperature range of from 600 degrees C. to 1200 degrees C. is usable for achieving a color tone.

These and further advantages will be explained in greater detail in the following with reference to an example of the method:

Commercially available alumina powder with a purity of 99.9% and a mean grain size of less than 2 $\mu$m is mixed with 0.05% by weight magnesia, 0.05% by weight yttria and 1% by weight polyvinyl alcohol as binder and spray-dried to form a granular material. A grain size of the granular material in the region of approximately 200 μm is obtained. The grain size of the granular material is preferably kept in the region of from 100 to 300 μm but this is not essential for the method itself.

A granular alumina material which has been thus doped and provided with agents for assisting the pressing is compacted uniaxially in a press to form the shaped bodies. Apart from the uniaxial cold pressing, isostatic pressing, injection molding or extrusion are also feasible.

The subsequent presintering is preceded by a period of slow heating during which the shaped bodies are heated up in the air to approximately 500 degrees C. in heating-up times which depending on the size of the shaped bodies are typically between 2 and 10 hours. During this time, the pores in the green body are open and form a substantially continuous pore volume. At the end of the preheating time, all of the agent for assisting the pressing has been burned out of the shaped body or green body so only the pure alumina shaped body, possibly with the doping material, is left over.

This is now followed by the actual presintering which is likewise carried out in the presence of atmospheric oxygen, with the shaped bodies being heated to a presintering temperature of 1600 degrees C. in as short a time as possible, i.e., preferably at a heating-up speed of $\geq 30$ degrees C./min.

At this temperature, relatively short holding times of approximately 30 minutes are adequate to obtain compaction at the surface with closed porosity. The temperature of 1600 degrees C. is not absolutely necessary as such closed porosity at the surface of the shaped body can already be achieved at substantially lower temperatures, i.e., already above 1400 degrees C. However, at these lower temperatures, the holding times for the presintering temperature are then longer.

These presintered parts are then recompacted in a commercially available hot isostatic press at temperatures of preferably 1600 degrees C. for approximately 30 minutes at a pressure of approximately 1000 bar, during which the residual porosity closes. In the case of the hot isostatic pressing, the heating-up time should again be selected as short as possible, i.e., less than one hour in order to prevent undesired grain growth.

With this method according to the invention, it was found surprising that doping of the alumina material is not absolutely necessary for the prevention of undesired grain growth, in order to achieve satisfactory transparency of the shaped body material.

Owing to the higher presintering temperature at which a closed porosity is achieved at the surface of the shaped body, which goes to the extent that the surface of the shaped body is gas-tight with respect to gases such as, for example, oxygen or nitrogen, the actual dense sintering in the hot isostatic press can be limited to a substantially lower temperature than is required in the prior art methods.

Owing to the substantially lower temperatures during the dense sintering, the speed of the grain growth is also substantially reduced during this procedure. Therefore, in particular for these reasons, the otherwise absolutely necessary doping agents can be readily dispensed with.

The present disclosure relates to the subject matter disclosed in German application No. P 38 11 902.1 of Apr. 9, 1988, the entire specification of which is incorporated herein by reference.

What is claimed is:

1. Method for the production of a shaped body of transparent, polycrystalline alumina, wherein a green body is formed in a first step using pure, fine-grained alumina with a purity of >99.0%, wherein pretreatment is carried out as a subsequent second step, and wherein compaction to transparent, polycrystalline alumina takes place in a third step, characterized in that a closed surface is produced on the shaped body during the pretreatment, in that pressure from all sides at elevated temperature is used in the third step to compact the shaped body, whereby residual porosity inside the shaped body is closed, and in that a yellowish color tone is imparted to said shaped body in a fourth step by annealing the compacted, transparent shaped body in air at a temperature above about 600° C.

2. Method as defined in claim 1, characterized in that a doping agent is added to the pure alumina during production of the green body.

3. Method as defined in claim 1, characterized in that the pretreatment comprises presintering.

4. Method as defined in claim 3, characterized in that a doping agent is added to the pure alumina during production of the green body.

5. Method as described in claim 3, characterized in that the presintering is carried out at a temperature above 1400 degree C.

6. Method as defined in claim 4, characterized in that the presintering is carried out at a temperature above 1400 degrees C.

7. Method as defined in claim 3, characterized in that the presintering is carried out in the presence of an oxygen-containing atmosphere.

8. Method as defined in claim 4, characterized in that the presintering is carried out in the presence of an oxygen-containing atmosphere.

9. Method as defined in claim 5, characterized in that the presintering is carried out in the presence of an oxygen-containing atmosphere.

10. Method as defined in claim 3, characterized in that the heating-up to the sintering temperature occurs very rapidly.

11. Method as defined in claim 5, characterized in that the heating-up to the sintering temperature occurs very rapidly.

12. Method as defined in claim 1, characterized in that the compaction in the third method step is achieved by hot isostatic pressing.

13. Method as defined in claim 12, characterized in that the temperature during the hot isostatic pressing is kept above 1400 degrees C.

14. Method as defined in claim 12, characterized in that the hot isostatic pressing is carried out in a protective gas atmosphere.

15. Method for the production of shaped bodies of transparent, polycrystalline alumina, wherein a green body is formed in a first step using pure, fine-grained alumina with a purity of >99.0%, wherein the green body is freed from binder agents used in its production by burning-out in a second step, wherein pretreatment is carried out as a subsequent third step, and wherein compaction to transparent, polycrystalline alumina takes place in a fourth step, characterized in that a closed surface is produced on the shaped body during the pretreatment, in that pressure from all sides at elevated temperature is used in the fourth step to compact the shaped body, whereby residual porosity inside the shaped body is closed, and in that a yellowish color tone is imparted to said shaped body in a fifth step by annealing the compacted, shaped body in air at a temperature above about 600° C.

16. Method as defined in claim 15, characterized in that a doping agent is added to the pure alumina during production of the green body.

17. Method as defined in claim 15, characterized in that the pretreatment comprises presintering.

18. Method as defined in claim 17, characterized in that a doping agent is added to the pure alumina during production of the green body.

19. Method as defined in claim 17, characterized in that the sintering is carried out at a temperature above 1400 degree C.

20. Method as defined in claim 18, characterized in that the presintering is carried out at a temperature above 1400 degrees C.

21. Method as defined in claim 17, characterized in that the presintering is carried out in the presence of an oxygen-containing atmosphere.

22. Method as defined in claim 18, characterized in that the presintering is carried out in the presence of an oxygen-containing atmosphere.

23. Method as defined in claim 19, characterized in that the presintering is carried out in the presence of an oxygen-containing atmosphere.

24. Method as defined in claim 17, characterized in that the heating-up to the sintering temperature occurs very rapidly.

25. Method as defined in claim 19, characterized in that the heating-up to the sintering temperature occurs very rapidly.

26. Method as defined in claim 15, characterized in that the compaction in the fourth method step is achieved by hot isostatic pressing.

27. Method as defined in claim 26, characterized in that the temperature during the hot isostatic pressing is kept above 1400 degrees C.

28. Method as defined in claim 26, characterized in that the hot isostatic pressing is carried out in a protective gas atmosphere.

* * * * *